United States Patent
Brechtelsbauer et al.

(10) Patent No.: US 6,482,960 B1
(45) Date of Patent: Nov. 19, 2002

(54) PROCESS FOR EPOXIDIZING SUBSTITUTED CYCLOHEXANONES

(75) Inventors: Clemens Michael Helmut Brechtelsbauer, Tonbridge (GB); Paul Oxley, Tonbridge (GB)

(73) Assignee: SmithKline Beecham p.l.c. (GB)

(*) Notice: Subject to any disclaimer, the term of this patent is extended or adjusted under 35 U.S.C. 154(b) by 0 days.

(21) Appl. No.: 10/069,703

(22) PCT Filed: Aug. 15, 2000

(86) PCT No.: PCT/EP00/07927
§ 371 (c)(1),
(2), (4) Date: Feb. 22, 2002

(87) PCT Pub. No.: WO01/14357
PCT Pub. Date: Mar. 1, 2001

(30) Foreign Application Priority Data

Aug. 25, 1999 (GB) .............................................. 9920152

(51) Int. Cl.[7] .............................................. C07D 303/12
(52) U.S. Cl. ...................................................... 549/332
(58) Field of Search ......................................... 549/332

(56) References Cited

FOREIGN PATENT DOCUMENTS

| WO | WO 98/34584 | 8/1998 |
|---|---|---|
| WO | WO 99/18793 | * 4/1999 |

* cited by examiner

Primary Examiner—Joseph K. McKane
Assistant Examiner—Jennifer C. Murphy
(74) Attorney, Agent, or Firm—James M. Kanagy; Charles M. Kinzig

(57) ABSTRACT

This invention relates to a method for preparing 1-oxaspiro [2,5]-carbonitriles from ketones using spinning disc reactor technology.

2 Claims, 1 Drawing Sheet

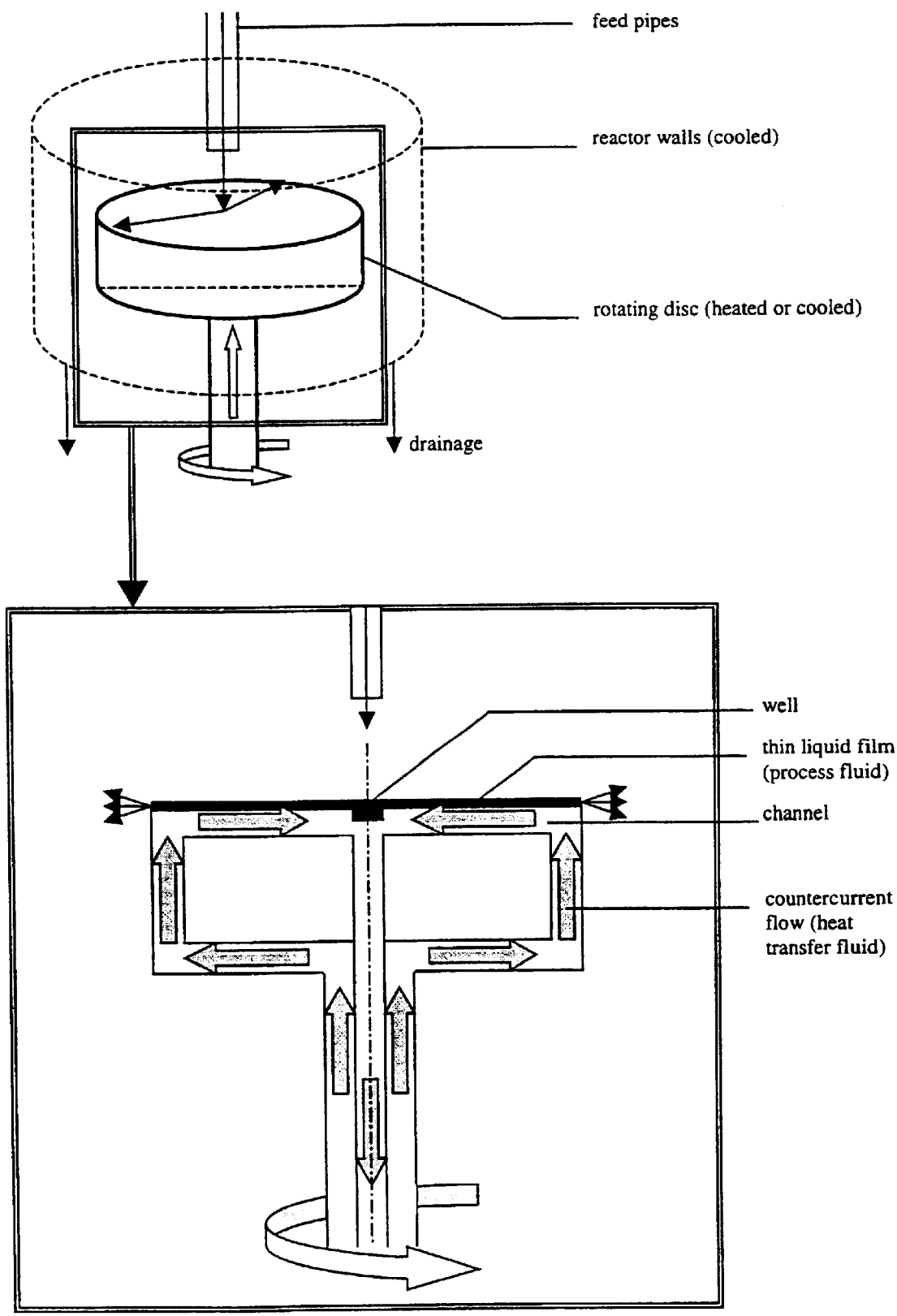
Figure I

PROCESS FOR EPOXIDIZING SUBSTITUTED CYCLOHEXANONES

SCOPE OF THE INVENTION

This invention relates to a novel process and in particular to a method for preparing 1-oxaspiro[2,5]-carbonitriles which can be used to make 4-substituted cyclohexanoic acids. The process, spinning disc reactor technology, also offers certain distinct advantages over traditional stirred tank reactors because of the reduced time of exposure of the carbonitrile to caustic which causes the carbonitrile to degrade to the amide.

AREA OF THE INVENTION

The process, its intermediates and products described by this invention provides a means for making certain 4-substituted4-(3,4disubstitutedphenyl)cyclohexanoic acids which are useful for treating asthma, and other diseases which can be moderated by affecting the PDE IV enzyme and its subtypes. The reaction utilizes a phase transfer catalysed Darzen's reaction. The products which can be made from the compound prepared herein are fully described in U.S. Pat. No. 5,552,483 issued Sep. 3, 1996. The information and representations disclosed therein, in so far as that information and those representations are necessary to the understanding of this invention and in its practice, are incorporated herein in total by reference.

SUMMARY OF THE INVENTION

This invention relates to a process for converting a substituted cyclohexan-1-one to a cis-(substituted)-1-oxobicyclo[2,5]octane-2-dicarbonitrile in the presence of base while minimizing the conversion of the 2 position nitrile to the amide comprising, in a spinning disc reactor (SDR):

i) preparing a first feed solution which comprises a 4-substituted cyclohexanone dissolved in an aqueous solvent ii) preparing a second feed solution which comprises an aqueous solution of chloroacetonitrile, inorganic base and an organic ammonium halide;

iii) feeding together the first and second feed solutions in amounts which give molar ratios of ketone and inorganic base on the disc of between about 1:2.8 to 1:15.9;

iv) said disc is spinning at between about 500 and 4800 revolutions per minute, and iv) having a residence time on the disc of between about 0.1 and 1 second.

In a second aspect, this invention relates to the compound 6Cyano-6-(3-cyclopentyloxy-4-methoxy-phenyl)-1-oxaspiro[2.5]octane-2-carboxylic acid amide or a composition containing same.

DESCRIPTION OF THE DRAWINGS

FIG. 1. A representation of a spinning disc reactor.

SPECIFIC EMBODIMENTS OF THE INVENTION

The spinning disc (FIG. 1) is a horizontally oriented plate that can be heated or cooled, and rotated at speeds of up to 5000 RPM. Liquid feed streams contacted in a well in the centre of the plate travel rapidly across the surface and form a thin film with thickness δ. Liquid leaves the disc at its edge after which it can be collected. The SDR is capable of subjecting this film to very high shear stress, $\tau$, promoting very high heat transfer rates between the film and the disc and high mass transfer rates between the liquid streams or the film and the gas in the surrounding atmosphere. Contact time, $t_{res.}$ on the disc is typically less than 1 s, therefore the reactor attains a steady state after 5–10 s of operation. The residence time characteristics of this system are ideally suited to the continuous processing of reactions with fast kinetics. In addition to this, the small hold up volume of the reactor (<100 mL) and the excellent temperature control of material on the disc make it particularly suited for highly exothermic, potentially hazardous reactions.

The currently available simplified model concept of the SDR is described in detail by (Saw, C. B., Anderson, G. K., Howarth, C. R., Porter, J. E., *Application of the spinning disc reactor as an ozone contactor*, Proc. Ind. Waste Conf. 40 (1985) 813–823, Boodhoo, K., Process Intensification: Spinning Disc Reactor for the Polymerisation of Styrene, PhD Thesis, Newcastle University 1999). It focuses on hydrodynamic aspects of a reactor with thin liquid film flow and provides correlations between operating conditions (such as spin speed, N and feed rate, $Q_v$), physical properties (such as density, ρ and viscosity, η) and Reynolds number, Re (flow regime), film thickness, δ, mean radial velocity, $v_{rel}$, and residence time, $t_{res}$.

A measure of the mixing efficiency in the liquid film can be obtained by calculating the shear stress, $\tau$, which is imposed on the liquid film by the rotation. The higher the shear stress, the more efficient the mixing. From the correlations described in (Saw, C. B., Anderson, G. K., Howarth, C. R., Porter, J. E., *Application of the spinning disc reactor as an ozone contactor*, Proc. Ind. Waste Conf. 40 (1985) 813–823, Boodhoo, K., Process Intensification: Spinning Disc Reactor for the Polymerisation of Styrene, PhD Thesis, Newcastle University 1999) it can be defined as:

$$\tau = -\eta \cdot \frac{v_{rel}}{\delta} = -\sqrt[3]{\frac{\eta \cdot \rho^2 \cdot Q_v \cdot \omega^4 \cdot r}{18\pi}} \quad (1)$$

Eqn. (1) immediately makes clear that the predominant influence on the shear stress is acted out by the angular velocity, ω, and therefore, by the rotational speed of the disc, N:

$$\omega = \frac{2 \cdot \pi \cdot N}{60} \quad (2)$$

This indicates that the mixing characteristics on the disc improve with increasing spin speed and are independent of laminar or turbulent flow of the film on the disc. Eqn. (3) shows, that the residence time on the disc is inversely proportional to the angular velocity, ω, and to the spin speed, N:

$$t_{res} = \left(\frac{81 \cdot \pi^2 \cdot \eta}{16 \cdot \omega^2 \cdot Q_v^2 \cdot \rho}\right)^{\frac{1}{3}} \cdot \left(r_0^{\frac{4}{3}} - r_i^{\frac{4}{3}}\right) \quad (3)$$

Thus, it is evident that increased mixing efficiency can only be realised at a very short contact time, which has important consequences for reactions limited by mass transfer. To observe effective conversion on the SDR, a high degree of conversion has to be achieved in reaction times shorter than 0.5 s.

An operational unit was fabricated in 316 stainless steel and comprised a 15 cm diameter disc mounted on a hollow assembly and housed in a jacketed cylinder of about 2 L volume. Interchangeable discs were fabricated from different materials (316 stainless steel or naval brass) and employed different surface textures (smooth, counterclockwise spiral groove or polytetrafluoroethylene coated). Heat transfer fluid, from an external, heated or cooled reservoir was pumped into the hollow disc assembly through a narrow channel (channel width 1 mm) directly beneath the disc to achieve the required disc operating temperature. The fluid then entered a collector, which drained back into the external heat exchanger. A lip seal between collector and rotating shaft assured complete separation of process and heat transfer side. Rotation of the disc up to 5000 RPM was achieved by use of an air motor and special rolling bearings, allowing for vertical and horizontal contraction/expansion of the shaft material with variation in operating temperature. Materials were fed onto the disc by two variable flow pumps, both peristaltic type and positive displacement Micropumps® being used. The reactor allowed a maximum throughput of 4.5 mL/second. Processed material left the reactor via two outlet drain pipes and could be sampled at two points immediately after exiting the SDR. The output was then collected in a cooled tank reservoir. Vapour formation was controlled by a condenser, which could either be arranged to collect condensate separately or return it to the SDR as required. Gaseous outlet was contacted in a suitable scrubber before release to the environment. Reactions were usually carried out under a nitrogen atmosphere.

Reagents were prepared as two separate feed solutions so that when mixed appropriately on the disc, the process of interest would start immediately. Critical stoichiometric ratios were controlled by measuring the concentrations of the feed solutions and adjusting the relative flow rates of each pump into the reactor.

Collected reaction samples were quenched immediately to halt further reaction and were analysed by HPLC according to adapted in-process check methods obtained from the respective batch process. The typical mode of operation of the SDR was as follows: The disc type was chosen and fitted. The reactor lid then closed and the whole set-up purged with nitrogen. The required temperature was set at the external heat exchanger and heat transfer fluid pumped through the disc assembly at about 6 L/minute. The disc speed was set by regulating the air motor and controlling the speed with a hand held optical tachometer. The desired feed ratios were identified, the pumps calibrated and set. Once material was detected leaving the reactor, the experiment commenced. A run lasted for up to 10 minutes with three samples being obtained during the experiment at regular time intervals. This was done in order to determine whether a steady state had been achieved during the run and also to obtain a degree of confidence in the reproducibility of the results. After this, the feed pumps were stopped. If necessary, the reactor was cleaned at this stage with a suitable solvent. The rotational speed was adjusted and another run commenced. On completion of this, either temperature, feed ratios, total feed rate or disc texture would be adjusted and the effect of disc speed re-evaluated.

The compounds which can be made from the compounds produced by the process of this invention are PDE IV inhibitors. They are useful for treating a number of diseases as described in U.S. Pat. No. 5,552,438 issued Sep. 3, 1996.

A representative schematic of this process is set out in Scheme I. This graphical representation uses specific examples to illustrate the general methodology used in this invention

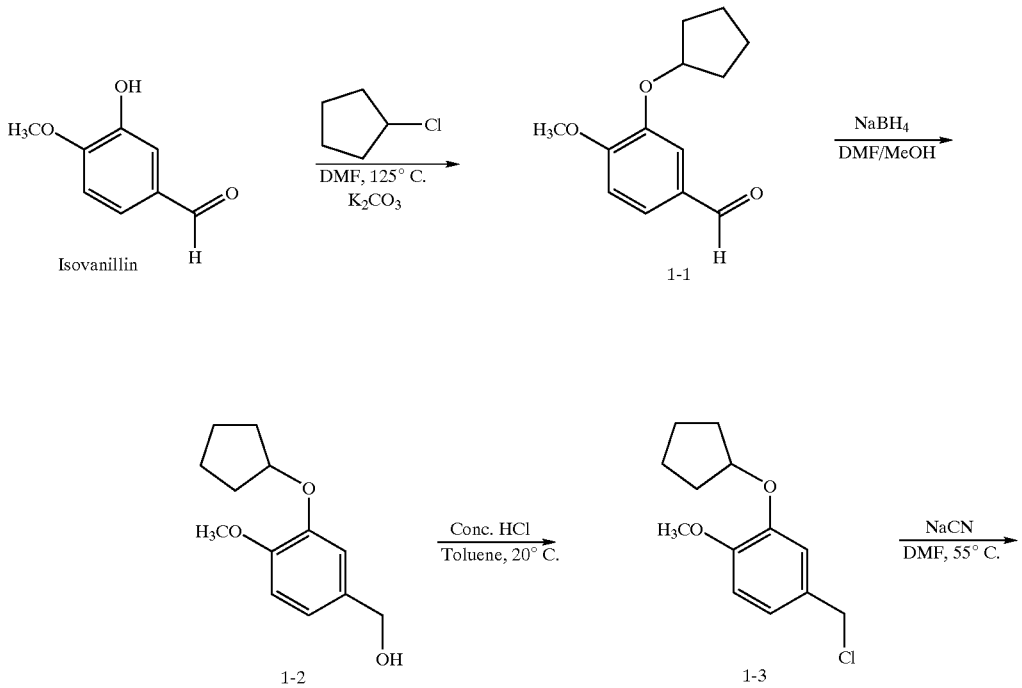

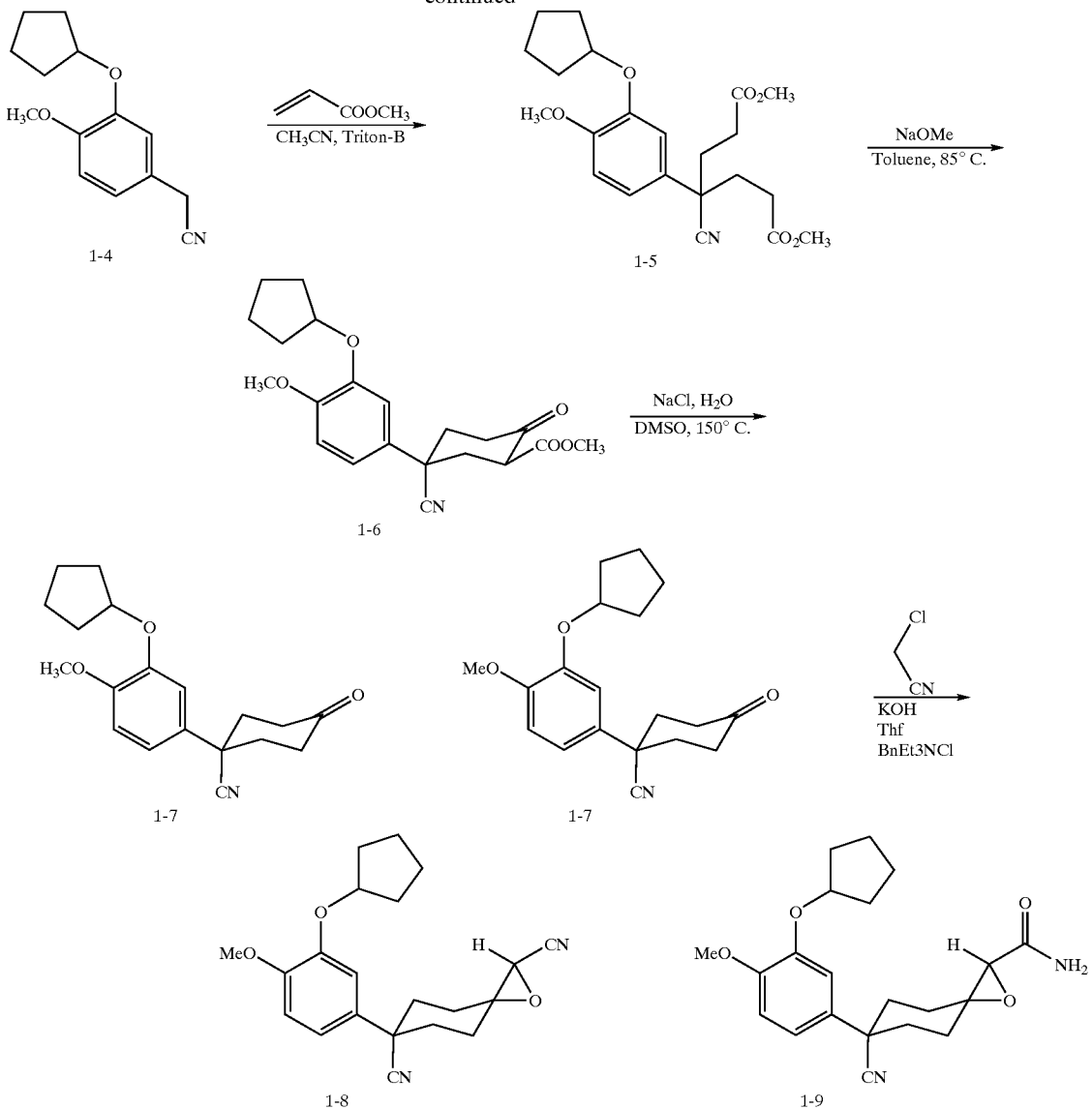

The application of spinning disc reactor (SDR) technology to this phase transfer catalysed Darzen's reaction in order to prepare 1-8 was investigated. For more on SDR technology see Jachuck, R. J.; Ramshaw, C.; Boodhoo, K. V. K.; Dalgleish, J. C. *Process Intensification: The Opportunity presented by Spinning Disc Reactor Technology;* Inst. Chem. Eng. Symp. Ser. 141 (1997) 417–424. As outlined above, the spinning disc is capable of subjecting a thin film of liquid to very high shear forces promoting very high heat transfer rates between the liquid and disc and high mass transfer rates between liquids or liquid and surrounding atmosphere.

A solution of ketone 1-7 and chloroacetonitrile in tetrahydrofuran and a solution of benzyltriethylammonium chloride in aqueous potassium hydroxide were mixed on the disc at various temperatures and stoichiometries whilst varying the rotational speed and disc texture.

Studies determined that a temperature of 20° C. was more effective than the typical batch process temperature 0° C. When operated at this higher temperature the reaction proceeded very rapidly on the disc, with a high conversion of the ketone occurring during the short contact time on the disc.

Further work showed that the extent of reaction is dependent on the rotational speed of the disc and the potassium hydroxide stoichiometry. Adding texture to the disc, in the form of a counter-clockwise spiral machined into the disc's surface, further increased the extent of reaction. The best result of nearly 90% conversion was achieved at high rotational speed with approximately 15 mole equivalents of caustic using a textured disc.

It should be noted that the contact time on the disc is inversely proportional to the disc's rotational speed and that the conversion increases with increasing disc speed. This means that, although the mixture has a shorter contact time on the disc at higher speeds, more reaction is achieved. This is consistent with the reaction rate being limited by the degree of mixing, which is well known for phase transfer reactions and demonstrates the ability of the SDR to impart high mass transfer through high shear at high rotational speeds. Without being bound by theory, the data suggests that the anion formation and reaction are extremely fast once the hydroxide ion has migrated to the organic phase with the rate limiting step being the rate of migration of the hydroxide anion into the organic phase. Using higher ratios of caustic to organic phase increases this rate.

The caustic used in this work is preferably an alkali metal hydroxide. Sodium hydroxide, potassium hydroxide or lithium hydroxide can be used. Potassium hydroxide is preferred. With regards to the organic ammonium halide, the preferred compound is benzyltriethylammonium chloride.

The following examples are provided to illustrate specific embodiments of the invention, not to limit it. What is reserved to the inventors is set forth in the claims appended hereto.

SPECIFIC EXAMPLES

Ketone 1-7 in Scheme I is made by the process set forth in WO 98/34584 or by the process set out in U.S. Pat. No. 5,552,483. Reference is made to those two publications for two illustrative examples of preparations of this ketone. The carbonitrile 1-8 can be converted to a corresponding cyclohexanoic acid by the process set forth in WO 98/34584.

Example 1

A batch process was carried out at 0° C., with 3 mole equivalents of potassium hydroxide. It was complete in around 1 hour. The process gave rise to 6-cyano-6-(3-cyclopentyloxy-4-methoxy-phenyl)-1-oxa-spiro[2.5]octane-2-carboxylic acid amide (compound 1-9 in Scheme 1 above) at around 1.5% caused by prolonged contact of 1-8 with the base. By comparison, when a reaction was run using spinning disc reactor technology with a contact time on the disc of under 1 second, less than 0.1% of the amide was formed.

Example 2

4-Cyano-4-(3-cyclopentyloxy-4-methoxyphenyl)cyclohexan-1-one was dissolved in THF and chloroacetonitrile in tetrahydrofuran was prepared, and potassium hydroxide and benzyltriethylammonium chloride in water are fed as separate streams into the centre of a heated or cooled, horizontal, rotating disc where the streams are intimately mixed and reaction occurs to produce cis-(+/−)-6-[3-(cyclopentyloxy)-4-methoxyphenyl]-1-oxaspiro[2.5]octane-2,6-dicarbonitrile and a minor amount of the acid amide (1-9).

Tetrahydrofuran was used to dissolve the ketone (0.71 moles/L) and chloroacetonitrile (0.86 moles/L).

The water was used to dissolve the potassium hydroxide (7.2–10.4 moles/L) and benzyltriethylammonium chloride (0.03–0.18 moles/L). This comprised the second feed solution.

These solutions were fed together into the SDR in varying amounts to achieve particular ratios of the ketone and potassium hydroxide on the disc (1:2.8–1:15.9). It is preferred that the ratio of ketone to benzyltriethylammonium chloride be about 1:0.047–0.057 (around 5 mole %)).

The temperature range investigated was −3° C. to +41° C.

The reaction time is predominantly dependent on the spin speed of the disc which was varied from 500 to 4800 rpm. Using eqn. (3), the calculated residence time on the disc is 0.1 to 0.8 seconds.

Yields were based on hplc analysis of the mixture. No product was ever isolated. Yields varied from 4% to 88% based on peak area ratio.

Conversion improved when a smooth disc was replaced by a disc with a grooved surface (counter-clockwise spiral). Yields were generally increased by 15% with this disc over a smooth disc under similar reaction conditions.

The best conditions used were with a ratio ketone:potassium hydroxide of 1:15, at high spin speed, at 20° C. and with the textured surface at 1.8 mL/second (108 mL/min).

Overall throughputs of the combined flow rates were 1.5–4.5 mL/sec (90–270 mL/min).

What is claimed is:

1. A compound which is 6-cyano-6-(3-cyclopentyloxy-4-methoxy-phenyl)-1-oxa-spiro[2.5]octane-2-carboxylic acid amide.

2. A composition which contains 6-cyano-6-(3-cyclopentyloxy-4-methoxy-phenyl)-1-oxa-spiro[2.5]octane-2-carboxylic acid amide.

* * * * *